United States Patent [19]

Forssen

[11] Patent Number: 4,946,683

[45] Date of Patent: Aug. 7, 1990

[54] MULTIPLE STEP ENTRAPMENT/LOADING PROCEDURE FOR PREPARING LIPOPHILIC DRUG-CONTAINING LIPOSOMES

[75] Inventor: Eric A. Forssen, La Canada, Calif.

[73] Assignee: Vestar, Inc., San Dimas, Calif.

[21] Appl. No.: 393,118

[22] Filed: Aug. 4, 1989

Related U.S. Application Data

[63] Continuation of Ser. No. 122,354, Nov. 18, 1987, abandoned.

[51] Int. Cl.$^5$ .............................................. A61F 13/00
[52] U.S. Cl. .................................. 424/422; 424/450; 428/402.2; 264/4.1
[58] Field of Search ............................... 424/422, 450; 428/402.2; 264/4.1

[56] References Cited

U.S. PATENT DOCUMENTS

| | | | |
|---|---|---|---|
| 3,993,754 | 11/1976 | Rahman et al. | 424/177 |
| 4,217,344 | 8/1980 | Vanlerberghe et al. | 424/60 |
| 4,235,871 | 11/1980 | Papahadjopoulos et al. | 424/19 |
| 4,241,046 | 12/1980 | Papahadjopoulos et al. | 424/19 |
| 4,263,428 | 4/1981 | Apple et al. | 536/17 A |
| 4,310,505 | 1/1982 | Baldeschwieler et al. | 424/1 |
| 4,330,534 | 5/1982 | Sakurai et al. | 424/182 |
| 4,331,654 | 5/1982 | Morris | 424/38 |
| 4,356,167 | 10/1982 | Kelly | 424/38 |
| 4,411,894 | 10/1983 | Schrank et al. | 424/199 |
| 4,419,348 | 12/1983 | Rahman et al. | 424/180 |
| 4,427,649 | 1/1984 | Dingle et al. | 424/38 |
| 4,438,052 | 3/1984 | Weder et al. | 264/4.6 |
| 4,515,736 | 5/1985 | Deamer | 264/4.3 |
| 4,619,794 | 10/1986 | Hauser | 264/4.1 |
| 4,769,250 | 9/1988 | Forssen | 424/450 |

FOREIGN PATENT DOCUMENTS

| | | |
|---|---|---|
| 0036676 | 9/1981 | European Pat. Off. . |
| 0004467 | 12/1981 | European Pat. Off. . |
| 0161445 | 11/1985 | European Pat. Off. . |
| 0198765 | 10/1986 | European Pat. Off. . |
| 8806442 | 9/1988 | European Pat. Off. . |
| 8500968 | 3/1985 | PCT Int'l Appl. . |
| 8505030 | 11/1985 | PCT Int'l Appl. . |
| 8601102 | 2/1986 | PCT Int'l Appl. . |
| 8601103 | 2/1986 | PCT Int'l Appl. . |
| 2146525 | 4/1985 | United Kingdom . |

OTHER PUBLICATIONS

Forssen et al., "Improved . . . Liposomes", Cancer Research 43, pp. 546–550, Feb. 1983.

Ryman et al., "Possible Use of Liposomes in Drug Delivery", Alfred Benzon Symposium 17, H. Bundgaard et al., ed., Copenhagen, 1982.

Ostro, ed., "Liposomes from Biophysics to Therapeutics", pp. 39–65, Marcel Dekker, Inc., N.Y., 1987.

Forssen et al., "Use of Anionic Liposomes for the Reduction of Chronic Doxorubicininduced Gardiotoxicity", Pro. Nat. Acad. Sci. U.S.A., vol. 78, No. 3, pp. 1873–1877, Mar./8.

Gabizon et al., "Liposomes . . . in Mice", Cancer Research, 44, 4734–4739, Nov. 1982.

Deamer et al. (1972), Biochim. Biophys. Acta 274, pp. 323–335.

Kornberg et al. (1972), Proc. Natl. Acad. Sci. U.S.A. 69 (6), pp. 1508–1513.

Nichols and Deamer (1976), Biochim. Biophys. Acta 455, pp. 269–271.

Casey et al., (1977) Biochemistry 16 (5), pp. 972–976.

Cramer and Prestegard (1977), Biochem. Biophys. Res. Commun. 75 (2), pp. 295–301.

Kano and Fendler (1978), Biochim, Biophys. Acta 509, pp. 289–299.

Mayer et al. (1986), Biochim. Biophys. Acta 857, pp. 123–126.

*Primary Examiner*—Brian E. Hearn
*Assistant Examiner*—Andy Griffis
*Attorney, Agent, or Firm*—Lyon & Lyon

[57] ABSTRACT

Novel liposome-entrapped cationic, lipophilic drug compositions, e.g., anthracycline antineoplastic agent compositions, and multistep entrapment/loading procedures for preparing them are disclosed. These procedures involve forming liposomes from phospholipids, such as distearoyl phosphatidylcholine or a similar long chain fatty acid diester phospholipid, to be loaded with the drug, e.g., daunorubicin or doxorubicin, in aqueous medium in the presence of an acid, e.g., an organic acid which can be monofunctional pyranosidyl acid such as lactobionic acid, adding the drug, and then adding a base such as calcium carbonate whose cations cannot pass through the vesicles' bilayers to charge neutralize the organic acid anions in the external aqueous phase and induce the acid anions in the internal aqueous phase to become neutralized by attracting the cationic, lipophilic drug.

27 Claims, No Drawings

MULTIPLE STEP ENTRAPMENT/LOADING PROCEDURE FOR PREPARING LIPOPHILIC DRUG-CONTAINING LIPOSOMES

This application is a continuation of application Ser. No. 122,354, filed Nov. 18, 1987, now abandoned.

This invention relates to novel liposome-entrapped lipophilic drug compositions, to methods of preparing such compositions, and to methods of using such compositions as chemotherapeutic agents to deliver the encapsulated drugs within the bodies of mammals, including humans.

More particularly, this invention relates to a novel multistep entrapment/loading procedure for incorporating any cationic, lipophilic drug which can partition into a lipid bilayer, and especially an anthracycline antineoplastic agent used to treat tumorous or malignant conditions in mammals, including humans, within liposome micellar particles which have been formed as unilamellar or multilamellar lipid vesicles. This novel entrapment/loading procedure facilitates the passage of the drug from the lipid membrane into the internal aqueous space within the liposome, thereby increasing entrapment efficiency and thus the amount of the drug deliverable within the body, e.g., the amount of an antineoplastic agent deliverable to tumor tissues. In the case of antineoplastic agents, the other benefits which have come to be associated with liposome-entrapped anthracycline antineoplastic agent therapy are also provided: increased in vivo stability for the drug delivery system, increased specificity of delivery of the drug to the tumor tissue site(s), decreased cardiotoxicity, and the ability to produce, and thus administer, these drug delivery systems on a large scale.

BACKGROUND OF THE INVENTION

The use of liposomes as biodegradable delivery systems for a variety of drugs, including their use to direct anthracycline antineoplastic agents to tumor tissue, increase the efficiency of the delivered anthracycline drug and reduce its cardiotoxicity, has been described in the scientific literature with increasing frequency for nearly twenty years. See for example Rahman et al U.S. Pat. No. 3,993,754, issued Nov. 23, 1976; Vanlergerghe et al U.S. Pat. No. 4,217,344, issued Aug. 12, 1980; Papahadjopoul et al U.S. Pat. No. 4,235,871, issued Nov. 25, 1980; Papahadjopoulos et al U.S. Pat. No. 4,241,046, issued Dec. 23, 1980; Apple et al U.S. Pat. No. 4,263,428, issued Apr. 21, 1981 ; Baldeschwieler et al U.S. Pat. No. 4,310,505, issued Jan. 12, 1982; Sakurai et al U.S. Pat. No. 4,330,534, issued May 18, 1982; Morris U.S. Pat. No. 4,331,654, issued May 25, 1982; Kelly U.S. Pat. No. 4,356,167, issued Oct. 26, 1982; Schrank et al U.S. Pat. No. 4,411,894, issued Oct. 25, 1983; Rahman et al 4,419,348, issued Dec. 6, 1983; Dingle et al U.S. Pat. No. 4,427,649, issued Jan. 24, 1984; Weder et al U.S. Pat. No. 4,438,052, issued Mar. 20, 1984and Deamer U.S. Pat. No. 4,515,736, issued May 7, 1985. Also, International Application No. PCT/US84/01431, published Mar. 4, 1985 (International Publication No. WO 85/00968) naming Mayhew et al as inventors; International Application No. PCT/US84/00855, published Nov. 21, 1985 (International Publication No. WO 85/05030) naming Janoff et al as inventors; European Patent Application No. 0,004,467, published Oct. 3, 1979 naming Apple et al as inventors; European Patent Application No. 0,036,676, published Sept. 30, 1981 naming Hunt et al as inventors; European Patent Application No. 0,161,445, published Nov. 21, 1985 naming Fukushima et al as inventors; European Patent Application No. 0,198,765, published Oct. 22, 1986 naming Rahman as inventor, and British Patent Application No. GB 2,146,525A, published Apr. 24, 1985 naming Margalit as inventor. Also, Ryman et al, "Possible Use of Liposomes in Drug Delivery", in "Optimization of Drug Delivery, Alfred Benzon Symposium 17" Ed. H. Bundgaard et al (Copenhagen: Munksgaard, 1982); Forssen et al, *Proc. Natl. Acad. Sci. USA*, 78, No. 3, 1873-1877 (1981); Gabizon et al, *Cancer Research*, 42, 4734-4739 (1982) and Forssen et al, *Cancer Research*, 43, 548-550 (1983).

One common drawback associated with prior art methods for preparing liposome drug delivery systems is the low levels of liposome drug entrapment ("trapping efficiency") achievable by such methods. International Patent Applications Nos. PCT/US85/01501 and PCT/USB85/01502, published Feb. 27, 1986 (WO86/01102 and WO6/01103) naming Bally et al as inventors, disclose methods which are reported to provide increases in trapping efficiencies approaching 100% entrapment while, at the same time, increasing the rate at which the drug is loaded into the liposome carrier. These methods involve generating a transmembrane potential creating an ionic gradient for one or more charged species—$Na+/K+$, $Ca++$ and $H+$ are disclosed—across the walls of the liposome. The concentration gradient, as the name implies, results from producing liposomes having different concentrations of charged species within ("the internal phase") and outside of ("the external phase") the vesicles. And see Ostro, Ed. "Liposomes, from Biophysics to Therapeutics" (New York: Marcel Dekker, Inc., 1987), pp. 60-65.

Adding acids, bases or both to control pH while carrying out processes designed to produce small unilamellar liposomes from specified lipid mixtures is disclosed in Hauser. U.S. Pat. No. 4,619,794, issued Oct. 28, 1986. The Hauser patent, however, does not disclose a method of loading drugs into preformed vesicles.

SUMMARY OF THE INVENTION

It has now been discovered that cationic, lipophilic drugs capable of partitioning into a lipid bilayer can be entrapped and loaded within typical liposome drug delivery systems rapidly and in high concentrations by a procedure which comprises, first of all, forming liposomes in aqueous medium in the presence of an organic acid:

which has at least one ionizable functional group, which is of sufficient polarity to be highly soluble in water, and which exhibits a low permeability throughout the vesicle membranes (i.e., a low leakage rate from the liposomes).

The drug being entrapped can be present while the liposomes are being formed or it can be added to the liposome-containing acidic aqueous medium (the external phase) subsequent to liposome formation, and in either case will become imbedded in but will not penetrate the membrane bilayer at this point in the process.

A base which will convert the acid molecules in the internal and external phases to the corresponding anions is then added. This base should be one whose cations cannot pass through the liposome vesicles' lipid bilayers, and the choice of a particular base will also be governed by the particular drug being entrapped. Certain bases have been found not to work, or to work less efficiently than others, in entrapping certain drugs, and particularly anthracycline antineoplastic agents.

The base cations charge neutralize the acid anions in the external aqueous phase. However, since the base cations are unable to pass through the lipid bilayer, acid anions contained in the internal aqueous phase within the vesicles can become charge neutralized only by combining with the cationic drug. Thus, the drug is induced to pass from the membrane bilayer into the internal aqueous phase.

It is, therefore, an object of this invention to provide novel cationic, liposome-entrapped lipophilic drug compositions, such as liposome-entrapped anthracycline antineoplastic agent compositions.

A further object of this invention is to provide a novel, multistep entrapment/loading method of preparing liposome-entrapped cationic, lipophilic drug compositions, such as liposome-entrapped anthracycline antineoplastic agent compositions, which facilitates the passage of the drug from the lipid membrane into the internal aqueous space within the liposome, thereby increasing entrapment efficiency and thus the amount of drug deliverable to the appropriate site(s) within the body.

These and other objects, as well as the nature, scope and utilization of this invention, will become readily apparent to those skilled in the art form the following description and the appended claims.

DETAILED DESCRIPTION OF THE INVENTION

Included among the cationic, lipophilic drugs which can partition into a lipid bilayer and which are thus suitable for use in practicing this invention are:

| Drug Class | Examples |
| --- | --- |
| Local anesthetics | Dibucaine, tetracaine, procaine, chlorpromazine |
| Cholinergic agents | Pilocarpine, physostigmine, neostigmine |
| Antimalarial agents | Chloroquine, amodiaquine, chloroguanide, primaquine, mefloquine, quinine |
| Antiparkinson agents | Pridinol, prodipine, benztropine mesylate, trihexyphenidyl hydrochloride |
| Antagonists for adrenergic receptors | Propranolol, timolol, pindolol |
| Antiprotazoates | Pentamidine, quinacrine |
| Antihistamines | Benadryl, promethazine |
| Biogenic amines | Dopamine, seratonin, epinephrine |
| General analgesics | Codeine, meperidine, methadone, morphine |
| Anticholenergics | Atropine, decyclomine, methixene, propantheline |
| Antidepressants | Imipramine, amitriptyline, doxepin, desipramine |
| Antiarrhythmic agents | Quinidine, propranolol, lidocaine |
| Antiemetics | Chloropromazine, promethazine, perphenazine |
| Ostro, op. cit., p. 64. | |

Cationic anthracycline compounds having antineoplastic activity against cancerous tissues or cells, including daunorubicin (also known as daunomycin), doxorubicin (also known as adriamycin), aclacinomycin A, vinblastine, vincristine, mitomycin C, and the like, are particularly preferred for incorporation within liposome micellar particles using the novel multistep entrapment/loading procedure of this invention. Structurally, these anthracycline compounds contain a hydrophobic tetracycline ring system coupled to an amino sugar through a glycoside linkage.

Biological lipids from which liposome bilayer membrane particles or vesicles useful in practicing this invention can be prepared are amphiphatic (hydrophobic and hydrophilic portion-containing) molecules which can spontaneously aggregate to form small spheres, ellipsoids or long cylinders, or bilayers having two or more parallel layers of amphiphatic molecules. In an aqueous (polar) medium, the polar heads of the amphiphatic molecules making up one layer orient outwardly to extend into the surrounding medium while the non-polar tail portions of these molecules likewise associate with each other. This provides a polar surface and a non-polar core in the wall of the vesicle. Such bilayered micelles usually take the shape of unilamellar (having one bilayer) or multilamellar (having a plurality of substantially concentric bilayers) spherical vesicles having an internal aqueous compartment.

Liposome bilayer membrane particles which have been found to be suitable in practicing this invention are small [e.g., from about 30 to about 150 nanometers (nm), and preferably from about 45 to about 60 nm, in diameter as determined, for example, using a light scattering particle sizer]neutral (uncharged or having balanced charges; i.e., zwitterions) unilamellar or multilamellar phospholipid vesicles or liposomes tailored to maximize entrapment/loading of a cationic, lipophilic drug by the method of this invention and to induce specificity and tissue/cell targeting, thereby maximizing uptake of the resulting liposome drug delivery system.

Liposomes suitable for use in practicing this invention can be prepared from carboxylic acid diesters of aliphatic triols and higher polyols, such as glycerol, sorbitol, mannitol, and the like, with glycerol being preferred, or of sphingosine or other amino alcohols containing long, unsaturated hydrocarbon chains, e.g., dialkyl amphiphiles such as sphingomyelin and the like, in which the ester moieties are derived from saturated or ethylenically unsaturated (from one to four, and preferably one or two unsaturated sites per chain) aliphatic monocarboxylic acids (long chain fatty acids) having from at least 14 to about 30 carbon atoms, and preferably from about 18 to about 24 carbon atoms, such as palmitic, stearic, 10-methylstearic, lignoceric, palmitoleic, oleic, linoleic, linolenic, phytanic and arachidonic acids and the like, and in which one or more, preferably one, of the polyol's hydroxy groups is substituted with a phosphate ester group which will itself be substituted with lower aliphatic dior higher functional compounds, generally lower aliphatic compounds having hydroxyl or amino (including substituted amino, e.g. lower alkyl substituted amino) groups, or both, such as ethanolamine, choline, serine, inositol, and the like.

Such liposome bilayer membrane particles include ones made from dipalmitoyl phosphatidylcholine, distearoyl phosphatidylcholine, dioleoyl phosphatidylethanolamine, distearoyl phosphatidylserine, dilinoleoyl phosphatidylinositol, distearoyl phosphatidylglycerol, and the like, or mixtures thereof. Liposome bilayer membrane particles made entirely from neutral phospholipids, such as distearoyl phosphatidylcholine, and preferably ones which have been further stabilized with cholesterol or like-acting substances, for example in a molar ratio of distearoyl phosphatidylcholine: cholesterol of about 2:1, respectively, have been found to be particularly suitable with regard to targeting efficiency when used to deliver anthracycline antineoplastic agents.

These liposomes are prepared by generally known techniques, such as the sonication method described in Mauk et al, *Anal. Bioc.* 94, 302–307 (1979) or by microemulsification using the procedure described in copending U.S. patent application Ser. No. 696,727, filed Jan. 31, 1985 in the name of R. Gamble and of common assignment with this application. Homogenization using a sonicator device will generally be carried out for from about 30 seconds to one minute per milliliter of suspension. Following homogenization, the suspension is centrifuged at from about 1,000 xg to about 20,000 xg, and preferably at about 5,000 xg, for from about 5 to 20 minutes, preferably about 10 minutes, at ambient temperature (usually about 22° C.), and then passed through a small pore diameter sterile filter, e.g., a 0.2–0.45 micron pore filter. These two steps (centrifugation and filtration) remove large particulate matter such as unsuspended lipids, large vesicles and other possibly contaminating particles.

The acid used when preparing liposomes in accordance with the present invention will, as mentioned above, be one which has at least one ionizable functional group, preferably at least one carboxyl group, is of sufficient polarity to be highly soluble in water (a solubility of at least about 0.01 Molar, and preferably more than about 0.10 Molar) and exhibits a low permeability or leakage rate from the liposomes formed in its presence.

Permeability or leakage can be measured by separating the vesicles from any material which has leaked out, using methods such as gel permeation chromatography, dialysis, ultrafiltration or the like, and assaying in known manner for any leaked material. Permeabilities ranging from about on to about ten percent of the original entrapped material over a period of about 24 hours or longer, and preferably less than about one percent of the original entrapped material over a period of about 24 hours or longer, are acceptable when practicing this invention.

The acids which in general can be used in practicing this invention are ones which will not hydrolyze the lipids in the vesicle formulation, and include organic acids, e.g., monofunctional pyranosidyl acids such as glucuronic acid, gulonic acid, gluconic acid, galacturonic acid, glucoheptonic acid, lactobionic acid, and the like, α-hydroxy polycarboxylic acids such as citric acid, iso-citric acid, hyaluronic acid, carboxypolymethylenes, and the like, amino acids such as glutamic acid, aspartic acid, carboxyaspartic acid, carboxyglutamic acid, and the like, saturated and unsaturated, unsubstituted and substituted aliphatic dicarboxylic acids such as succinic acid, glutaric acid, ketoglutaric acid, tartaric acid, galactaric acid, maleic acid, fumaric acid, glucaric acid, malonic acid, and the like, phosphorus-containing organic acids such as phytic acid, glucose phosphate, ribose phosphate, and the like, and inorganic acids, e.g., sulfonic acid, sulfuric acid, phosphoric acid, polyphosphoric acids, and the like.

The pyranosidyl acids have been found to be most effective for anthracycline antineoplastic agent loading by the method of this invention, inasmuch as doxorubicin, which has been found to be entrapped with more difficulty than daunorubicin by this method, is readily entrapped by lactobionic and galacturonic acids but not by acetic acid. Citric acid has also been found to entrap doxorubicin, but surprisingly the resulting loaded vesicles proved to be far more toxic than the free drug. In nearly all instances of vesicle-entrapped doxorubicin reported in the literature, the loaded vesicles are less toxic than the free drug.

The base which will convert the acid molecules in the internal and external aqueous phases to the corresponding anions should, as mentioned above, be one whose cations cannot pass through the vesicles' lipid bilayers. Included among such bases are alkali and alkaline earth metal hydroxides, carbonates and like compounds, e.g., sodium, potassium, lithium, calcium and magnesium hydroxides and carbonates, and amines such as N-methylglucamine, ethylene diamine and TRIS base [also known as tromethamine, 2-amino-2-hydroxymethyl-1,3-propanediol and tris (hydroxymethyl)aminomethane], all of which have high solubility in water—greater than 0.01 Molar—and are of low solubility 'less than 0.01mMolar—or insoluble in organic solvents such as ethanol, chloroform, diethyl ether and ethyl acetate.

As was the case with the acid, certain of the bases which meet this criterion of having cations which cannot pass through the vesicles'lipid bilayers have been found to be more effective than others for anthracycline antineoplastic agent loading by the method of this invention. Carbonates, such as calcium carbonate, sodium carbonate, sodium bicarbonate, and the like have been found to work in all cases, including for the difficultly entrappable doxorubicin. Basic hydroxides, such as sodium, potassium and calcium hydroxide, and amines, including ethylene diamine, TRIS and N-methylglucamine all were not effective for loading doxorubicin into vesicles by the method of this invention.

In practicing the method of this invention the vesicles, e.g., as dry powders if stored in this form, are first dispersed in aqueous medium at a temperature of from about 40° C. to about 80° C., preferably from about 50° C. to about 70° C., at a vesicle concentration of from about 5 mg/ml to about 100 mg/ml, and preferably at from about 20 mg/ml to about 40 mg/ml. Water alone, preferably although not necessarily deionized (small anions such as chloride, which can easily pass through the bilayer membrane, may interfere with the entrapment/loading procedure) may be used, or other low ionic media such as the aqueous sugar solutions disclosed in copending U.S. patent application Ser. No. 787,535, filed Oct. 15, 1985 in the name of Eric Forssen and of common assignment with this application.

As mentioned above cholesterol and like-acting substances, e.g., other sterols, zwitterionic or charged lipids, and the like, can be added, if desired, to the aqueous vesicle dispersion to further improve the stability of the subsequently-formed drug-loaded vesicles. Such substances ordinarily will be added in amounts ranging from about 0.1 to about 50 mol percent, and preferably from about 5 to about 33 mol percent, based on the total amount of the components of the bilayer membrane.

The chosen acid used when preparing the aqueous vesicle-containing medium will be present during hydration and homogenization (e.g., sonication) and before addition of the drug being loaded, and will be employed in concentrations ranging from about 10 mMolar (millimolar) to about 300 mMolar, and preferably from about 50 mMolar to about 200 mMolar, with the suspension being held at a temperature of from about 30°C. to about 70° C., and preferably at from about 50° C. to about 60° C., during this step.

The drug, e.g. an anthracyclic antineoplastic agent, will be added to the acidic aqueous vesicle-containing medium either as a dry powder or, preferably, as a concentrated solution in water, in amounts ranging from about 1 mg/100 mg lipid to about 10 mg/100 mg lipid, and preferably from about 1 mg/20 mg lipid to about 1 mg/30 mg lipid, in order to insure as close to 100% entrapment as possible. The temperature at which the drug is added will generally be above the phase transition temperature of the vesicles, e.g., a temperature of from about 40° C. to about 80° C., and preferably from about 50° C. to about 65° C., to facilitate diffusion of the drug into the vesicles, and the drug-containing suspension will preferably be held at that temperature during subsequent base addition.

The selected base will be added to the drug-containing acidic vesicle suspension in amounts ranging from about one-sixth mol equivalent to about one mol equivalent, based on the net ionization of the acid and the final pH desired. In the case of anthracycline antineoplastic agent-containing suspensions, a pH ranging from about 4.5 to about 6.0 will usually be achieved. Base addition will ordinarily be carried out while continuing to heat the mixture, e.g., at a temperature of from about 40° C. to about 80° C., over a period of from about one to about ten minutes, preferably while agitating the mixture to produce rapid and thorough mixing. Following base addition, heating will ordinarily be continued for another 5 to 20 minutes, preferably about 10 minutes.

The time periods within which each of these method steps and the overall entrapment/loading procedure are carried out are, however, not critical. The overall method, including subsequent workup procedures to ready the drug delivery systems for parenteral administration, e.g., for human intravenous injection, or for storage until used will ordinarily take from about 30 to about 120 minutes.

Such workup procedures can include, first of all, removal of the acid or other anions from the aqueous environment external to the liposomes and its replacement with, e.g., an aqueous solution of a sugar, e.g., a solution containing from about 5% to about 20% by weight of a biologically acceptable mono-, di- or trisaccharide compatible with the drug-filled vesicles, such as lactose, dextrose, sucrose, trehalose, raffinose, maltose, or the like, or such a solution containing a non-saccharide polyol such as glycerol, inositol, sorbitol, mannitol, or the like, and also containing from about 0.1% to about 2% by weight of an excipient such as glycine, tromethamine, n-methylglucamine, or the like, which functions as a buffer. This removal of the acid or other anions from the external aqueous medium can be accomplished using gel permeation chromatography, ultrafiltration, vacuum dialysis, tangential flow filtration, hollow fiber filtration or like methods, with gel permeation chromatography being preferred for volumes of product of 100 ml or less and tangential flow filtration for volumes in excess of 100 ml.

Acid replacement is ordinarily followed by centrifugation and concentration, again using vacuum dialysis, ultrafiltration, tangential flow filtration or other methods designed to remove water and aqueous solutes while retaining the lipid vesicles and their contents.

In order that those skilled in the art can more fully understand this invention, the following examples are set forth. These examples are given solely for purposes of illustration, and should not be considered as expressing limitations unless so set forth in the appended claims. All parts and percentages are by weight, unless otherwise stated.

EXAMPLE I

Entrapment of daunorubicin in distearoyl phosphatidylcholine-cholesterol vesicles using citric acid and sodium hydroxide.

A dry powder containing a homogenous dispersion of cholesterol in distearoyl phosphatidylcholine at a 1:2 molar ratio is prepared. This dispersion is then hydrated with an aqueous solution containing 41/2% lactose (equivalent to 125 mMolar) and 50 mM citric acid at a pH of about 2.0 to 2.5 (not adjusted). The concentration of lipid in the resulting suspension is 20 mg per ml. This mixture is heated to 65° C. Next, while holding that temperature, the mixture is vigorously homogenized using a sonicator, a device which produces a high shear force, until a suspension of small, unilamellar vesicles is produced. The thus-obtained vesicles are in the range of about 40 to 60 nm in diameter, with little or no material in excess of 100 nm. Vesicle size is determined using a Nicomp laser light scattering particle sizer. The duration of homogenization is about one minute per milliliter suspension.

Following the homogenization procedure, the preparation is centrifuged at about 5,000xg for 10 minutes at ambient temperature. Next the material is passed through a 0.2 micron pore diameter sterile filter.

The vesicle preparation is then heated again to about 65° C. and an amount of daunorubicin is added as a concentrated solution in water sufficient to yield a final daunorubicin concentration of about 1.0 mg/ml. Next, while continuing to heat the mixture, an amount of sodium hydroxide equal to two and one-half mole equivalents per mole of citric acid is added to the mixture over a period of about three minutes. The suspension is then vigorously agitated to produce rapid and thorough mixing. Following the addition of sodium hydroxide, the mixture is incubated at the same temperature for about 10 minutes. At this stage in the procedure, the daunorubicin has transversed the bilayer membrane to the vesicle interior and formed a salt with citrate as the counterion. After the incubation period, the mixture is cooled to ambient temperature and centrifuged as described previously. Next, the exterior aqueous phase, containing citrate and sodium ions, along with any unentrapped daunorubicin if present, is exchanged for a solution of 9% lactose in water with 50 mMolar glycine by gel permeation chromatography.

Following this exchange procedure, the drug containing vesicles are concentrated to about 40 mg/ml (equivalent to 2 mg/ml daunorubicin). Concentration can be accomplished by tangential flow filtration, which removes water and aqueous solutes while retaining the lipid vesicles and their contents. This concentrated product is then sterilized by filtration through 0.45 micron diameter pore filters. The finished lipid vesicle suspension containing entrapped daunorubicin is then ready for use or may be stored for four or more weeks frozen, or at from 4° C. to 22° C.

EXAMPLE II

The procedure of Example I above is repeated in every essential detail except for the following:
 sodium hydroxide is replaced with an equivalent amount of sodium bicarbonate;
 an equivalent amount of tartaric acid is used in place of citric acid;

the exchange procedure is carried out with an aqueous 11% lactose solution in place of the aqueous 9% lactose/50 mMolar glycine solution.

A lipid vesicle suspension containing entrapped daunorubicin is again obtained.

EXAMPLE III

Entrapment of doxorubicin using distearoyl phosphatidylcholine, cholesterol, lactobionic acid and calcium carbonate.

A dry powder containing a homogenous dispersion of cholesterol in distearoyl phosphatidylcholine in a 1:2 mole ratio is prepared. This dispersion is then hydrated with an aqueous solution of 200 mMolar lactobionic acid in water (71.66 gm/liter) with a pH of 2.0 to 2.5 (not adjusted). The lipid concentration in the resulting suspension is about 20 mg/ml. This mixture is then heated to 70° C. The preparation is then homogenized, centrifuged and filtered as described in Example I hereinabove.

After the suspension of small, unilamellar vesicles in 200 mMolar lactobionic acid has been prepared, it is heated to 65° C. and amount of doxorubicin is then added, as a concentrated solution in water, which will result in a final doxorubicin concentration of about 1.0 mg/ml. Next, while continuing to heat the mixture, calcium carbonate is added as a dry powder in an amount equivalent to about 20 grams per liter. Heating is continued for an additional 10 minutes, during which time the preparation is vigorously agitated. Next the mixture is centrifuged to remove excess calcium carbonate and other precipitated materials. The remaining processing steps are as described in Example I hereinabove.

A lipid vesicle suspension containing entrapped doxorubicin is obtained.

EXAMPLE IV

The procedure of Example III above is repeated in every essential detail except for the following:
galacturonic acid is used in place of lactobionic acid; calcium carbonate is replaced by sodium carbonate.

A lipid vesicle suspension containing entrapped doxorubicin is again obtained.

EXAMPLE V

The procedure of Example III above is again repeated in every essential detail but one. Distearoyl phosphatyidylglycerol, cholesterol and distearoyl phosphatidylcholine are included in the vesicle bilayer in a mol ratio of about 1.5:5:10, respectively.

A lipid vesicle suspension containing entrapped doxorubicin is again obtained.

EXAMPLE VI

Daunorubicin vesicles, prepared as described in Example I hereinabove, were stored frozen, refrigerated at 4° C., or at room temperature (22° C.). At two and four weeks, the samples were assayed for: (1) chemical stability of the drug and lipid components, (2) retention of drug within the vesicles, and (3) biological activity as measured by antitumor activity (two weeks only). No significant degradation or loss of drug or of vesicle lipids could be detected out to four weeks. There also appeared to be no significant leakage except for possibly about a 5% leakage of drug from frozen and thawed vesicles. Biological activity was superior to freshly prepared free daunorubicin and slightly less than (4° C. storage) or superior to (frozen and stored at 22° C.) freshly prepared vesicles.

EXAMPLE VII

Antitumor activity of daunorubicin vesicles.

Daunorubicin vesicles prepared as described in Example I hereinabove have been tested against P-1798 lymphosarcoma and Ma16c mammary adenocarcinoma, both solid tumors in mice. The studies with the Ma16c tumor are still in progress; the P-1798 tumor studies have been completed. Treatments at all dose levels, ranging from 10 mg/kg to 50 mg/kg, have demonstrated that when formulated as described above daunorubicin vesicles have more antitumor activity and less toxicity, as determined by increased life span and reduced tumor size, than the parent drug.

EXAMPLE VIII

Biological activity of doxorubicin vesicles.

Doxorubicin vesicles prepared as described in Examples III and IV have been tested for toxicity and antitumor activity. These studies are still continuing, however, some results and conclusions are now evident.

Treatment of $CD_2F_1$ mice has indicated that the maximum tolerated dose (MTD, non-lethal) of a single intravenous dose of the free drug, doxorubicin hydrochloride, is about 25 mg/kg. This compares to an MTD of about 40 mg/kg (normalized to the hydrochloride) for doxorubicin vesicles prepared as described in Example III. In contrast, the MTD for doxorubicin vesicles, when prepared as described in Example III with the exception that citric acid was substituted for lactobionic acid, was only about 10 mg/kg, less than the MTD for the free drug.

Doxorubicin vesicles prepared with lactobionic acid have demonstrated less toxicity as measured by suppression of white blood cells and by survival at high doses as compared to free drug.

White blood cell (w.b.c.) counts were performed on $CD_2F_1$ mice receiving doxorubicin doses of 40 mg/kg (for the equivalent hydrochloride). Mice receiving free drug experienced severe depression in w.b.c. counts: at four days post therapy, counts were only 8.5% of pretherapy values. In contrast, mice treated with doxorubicin vesicles prepared in accordance with this invention (Example III) at the same doxorubicin dosage experienced only moderate suppression in w.b.c. counts: at four days post therapy, counts were 75% of pretherapy values.

Doxorubicin vesicles can also be prepared with citric acid. However, intravenous tests in mice have demonstrated that while free drug doses of 20 mg/kg are tolerated, equivalent doses of doxorubicin citrate in vesicles are lethally toxic.

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

I claim:

1. A method of preparing a phospholipid-entrapped cationic, lipophilic drug composition which comprises:
   a. forming liposomes in an aqueous medium containing an acid which has at least one ionizable functional group, is of sufficient polarity to be highly soluble in water and exhibits a low permeability through the vesicle membranes to give an acidic liposome-containing aqueous medium in which the acid is present in the internal and external liposome phases, said liposome being prepared from hydroxyamino(lower)aliphatic-substituted phosphatidyl carboxylic acid diesters of a tri- or higher functional aliphatic polyol in which the ester moieties are derived from a saturated or ethylenically unsaturated aliphatic monocarboxylic acid having at least 14 carbon atoms, b. adding to the thus-obtained acidic liposome-containing aqueous medium a cationic, lipophilic drug, and c. then adding a base whose cations cannot pass through the liposomes' lipid bilayers to charge neutralize the acid anions in the external aqueous phase, thereby inducing the cationic, lipophilic drug to pass into the liposomes' internal aqueous phase.

2. A method as recited in claim 1 in which said liposomes are formed from distearoyl phosphatidylcholine.

3. A method as recited in claim 1 in which said liposomes include distearoyl phosphatidylglycerol.

4. A method as recited in claim 1 in which said acid is an organic acid.

5. A method as recited in claim 4 in which said organic acid is a monofunctional pyranosidyl acid.

6. A method as recited in claim 5 in which said pyranosidyl acid is lactobionic acid.

7. A method as recited in claim 4 in which said organic acid is an amino acid.

8. A method as recited in claim 4 in which said organic acid is an α-hydroxy polycarboxylic acid.

9. A method as recited in claim 4 in which said organic acid is a dicarboxylic acid.

10. A method as recited in claim 1 in which said base is an alkali or alkaline earth metal hydroxide or carbonate.

11. A method as recited in claim 10 in which said base is sodium hydroxide.

12. A method as recited in claim 10 in which said base is sodium bicarbonate.

13. A method as recited in claim 10 in which said base is calcium carbonate.

14. A method as recited in claim 1 in which said base is an amine.

15. A method as recited in claim 14 in which said amine is N-methylglucamine.

16. A method as recited in claim 14 in which said amine is tris(hydroxymethyl)aminomethane.

17. A method as recited in any one of claims 1–16, inclusive, in which cholesterol is present in the lipsome bilayers as a stabilizer.

18. A method as recited in claim 17 in which, following the addition of the base, the acid and other anions are removed from the aqueous environment external to the liposomes and replaced with an aqueous sugar solution.

19. A method as recited in claim 18 in which said sugar is lactose.

20. A method as recited in claim 1 in which said cationic, lipophilic drug is an anthracycline antineoplastic agent.

21. A method as recited in claim 20 in which said anthracycline antineoplastic agent is daunorubicin.

22. A method as recited in claim 20 in which said anthracycline antineoplastic agent is doxorubicin.

23. A method as recited in claim 1 in which said acid is citric acid, said base is sodium hydroxide, said diester is distearoyl phosphatidylcholine, said cationic, lipophilic drug is daunorubicin and cholesterol is present in the lipsome bilayers as a stabilizer.

24. A method as recited in claim 23 in which the molar ratio of distearoyl phosphatidylcholine to cholesterol is about 2:1.

25. A method as recited in claim 1 in which said acid is lactobionic acid, said base is calcium carbonate, said diester is distearoyl phosphatidylcholine, said cationic, lipophilic drug is doxorubicin and cholesterol is present in the liposome bilayers as a stabilizer.

26. A method as recited in claim 25 in which the molar ratio of distearoyl phosphatidylcholine to cholesterol is about 2:1.

27. A method as recited in claim 1 in which said acid is galacturonic acid, said base is sodium carbonate, said diester is a mixture of distearoyl phosphatidylglycerol an distearoyl phosphatidylcholine, said cationic, lipophilic drug is doxorubicin and cholesterol is present in the lipsome bilayers as a stabilizer.

* * * * *

Adverse Decisions In Interference

Patent No. 4,946,683, Eric A. Forssen, MULTIPLE STEP ENTRAPMENT/LOADING PROCEDURE FOR PREPARING LIPOPHILIC DRUG-CONTAINING LIPOSOMES, Interference No. 103,469, final judgment adverse to the patentee rendered May 19, 1998 as to claims 1-4 and 7-24.
*(Official Gazette July 7, 1998)*